United States Patent [19]

Hänel et al.

[11] Patent Number: 5,118,500
[45] Date of Patent: Jun. 2, 1992

[54] PHARMACEUTICAL CONTAINING TNF INHIBITOR

[75] Inventors: Heinz Hänel, Oberursel; Elmar Schrinner, Wiesbaden, both of Fed. Rep. of Germany

[73] Assignee: Hoechst Aktiengesellschaft, Frankfurt am Main, Fed. Rep. of Germany

[21] Appl. No.: 356,734

[22] Filed: May 25, 1989

[30] Foreign Application Priority Data

May 27, 1988 [DE] Fed. Rep. of Germany ....... 3817955

[51] Int. Cl.$^5$ .................... A61K 45/05; A61K 37/00; A61K 39/00
[52] U.S. Cl. .................... 424/85.1; 514/21; 424/88
[58] Field of Search ........................ 424/85.1

[56] References Cited

U.S. PATENT DOCUMENTS 4,879,111 11/1989 Chong ................................. 424/85.2

OTHER PUBLICATIONS

C. M. Lilly et al., American Review of Respiratory Disease, vol. 137, No. 4, Part 2, Apr. 1988, p. 138, New York, US.
R. M. Strieter et al., Biochemical and Biophysical Research Communications, vol. 155, No. 3, Sep. 1988, pp. 1230–1236, New York, US.
Clinical Hemorheology, vol. 6, pp. 455–467 (1986).
Drugs of the Future, vol. 12, pp. 891–898 (1987).
Nature, vol. 330, pp. 662–664 (1987).

*Primary Examiner*—Christine Nucker
*Assistant Examiner*—Lynette F. Smith
*Attorney, Agent, or Firm*—Finnegan, Henderson, Farabow, Garrett and Dunner

[57] ABSTRACT

Pharmaceuticals which contain a substance releasing tumor necrosis factor (TNF) are better tolerated and can be given in higher doses when they contain a TNF inhibitor, especially a xanthine derivative.

20 Claims, No Drawings

PHARMACEUTICAL CONTAINING TNF INHIBITOR

BACKGROUND OF THE INVENTION

It is known that the definition of the term tumor necrosis factor (TNF) includes two cytotoxic factors (TNF-α and TNF-β) which are essentially formed by activated lymphocytes and monocytes. The term TNF derives from the property which initially attracted particular attention from those skilled in the art: TNF has a necrotic effect on certain tumors in vivo. This effect was found for the first time when it was observed that, in cases of cancer, bacterial infections may result in a regression of the tumor. It was initially assumed that lipopolysaccharides from the cell walls of bacteria, which are called endotoxin, are responsible for the regression of the tumor. However, it was later shown that the endotoxin itself had no direct antitumor effect but in turn induces the formation of a factor which is responsible for the tumor necrosis. This factor was then called TNF. Further investigations later revealed that TNF is principally formed by macrophages. It was likewise shown, by stimulation of lymphocytes in vitro, that there is formation of a substance having cytotoxic activity, which was called lymphotoxin. The close relationship between TNF and lymphotoxin was only recently discovered after the two proteins had been prepared in pure form, their primary structure had been established and their cDNAs had been isolated and expressed. This revealed remarkable similarities in the two proteins and their genes. Great similarities were also evident from the biological activities of these two proteins. For this reason, they were called TNF-α and TNF-β, corresponding to their formation from monocytes or lymphocytes.

Once relatively large amounts of TNF became available by application of methods of genetic manipulation for the preparation, it emerged that, besides its antitumor effect, TNF also has a large number of other effects. They are described in detail by Bharat B. Aggarwal in "Drugs of the Future" 12 (1987), pages 891 et seq. Overall, it has to be stated that TNF carries out an important task in the immune system of the body but that there may be overproduction of TNF in certain infections, diseases or injuries, and this may be life-threatening. For this reason, there has also already been a proposal that a TNF inhibitor be used in certain pathological states where there is overproduction of TNF. Monoclonal antibodies directed against TNF have already been proposed for this purpose (Nature, vol. 330, pages 662 et seq.). Moreover, it has already been disclosed that shock induced by endotoxin can be prevented by previous administration of pentoxifylline (Clinical Hemorheology, vol. 6, 1986, pages 455-467).

DETAILED DESCRIPTION OF THE PREFERRED EMBODIMENTS

The present invention is now based on the idea that intolerance of certain pharmaceuticals may possibly be caused by administration thereof being followed by release of such large amounts of TNF in the body that necroses or other side effects arising from overproduction of TNF occur. This idea has been confirmed by investigations with the antimycotic amphotericin B, which is known to result in 100 % lethality after parenteral administration in animal experiments if certain amounts of active substance are exceeded. However, if amphotericin B is administered together with a TNF inhibitor the amphotericin B, which is otherwise highly toxic, is tolerated without side effects.

Hence the invention relates to a pharmaceutical which, besides a substance releasing tumor necrosis factor (TNF), also contains a TNF inhibitor. Xanthine derivatives have proven to be suitable TNF inhibitors.

Preferred xanthine derivatives derive from the following group of compounds:

1) Compounds of the formula I

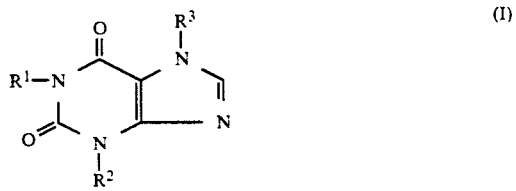

in which one of the radicals $R^1$ and $R^3$ represents a straight-chain alkyl, (ω-1)-oxoalkyl or (ω-1)-hydroxyalkyl group having 3 to 8 carbon atoms, and the two other radicals, $R^2$ and $R^3$ or $R^1$ and $R^2$, represent straight-chain or branched alkyl groups having 1 to 8 carbon atoms in the position of $R^1$ and $R^3$ and 1 to 4 carbon atoms in the position of $R^2$, where the total of carbon atoms in these two alkyl substituents does not exceed 10, 2) compounds of the formula II

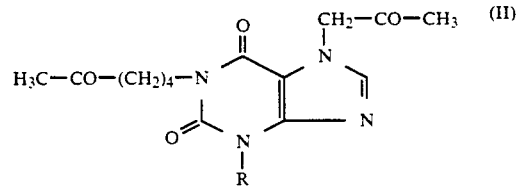

in which R represents an alkyl radical having 1 to 4 carbon atoms, 3) compounds of the formula III

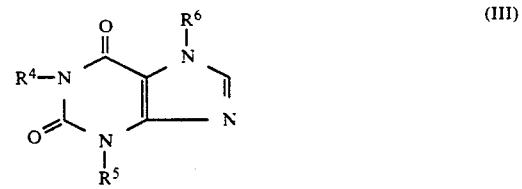

in which at least one of the radicals $R^4$ and $R^6$ represents a tertiary hydroxyalkyl group of the formula

where $R^7$ denotes an alkyl group having up to 3 carbon atoms, and n denotes an integer from 2 to 5, and—if only one of the radicals $R^4$ or $R^6$ denotes such a tertiary hydroxyalkyl group of the formula IIIa—the other radical represents a hydrogen atom or an aliphatic hydrocarbon radical $R^8$ which has up to 6 carbon atoms and whose carbon chain can be interrupted by up to 2 oxygen atoms or substituted by an oxo group or up to two hydroxyl groups (in which case an oxo or hydroxyl group present in the radical $R^8$ is preferably separated from the nitrogen by at least 2 carbon atoms), and $R^5$ represents an alkyl group having 1 to 4 carbon atoms, 4) prodrug forms of the compounds of the formulae I to III, and/or 5) metabolites of the compounds of the formulae I to III.

In turn, those among these compounds which are particularly preferred have the formula I with a hexyl, 5-oxohexyl or 5-hydroxyhexyl group in the position of $R^1$ or $R^3$. These include, in particular, 1-hexyl-3,7-dimethylxanthine, 1-(5-hydroxyhexyl)-3,7-dimethylxanthine, 3,7-dimethyl-1-(5-oxohexyl)xanthine, 7-(5-hydroxyhexyl)-1,3-dimethylxanthine, 1,3-dimethyl-7-(5-oxohexyl)xanthine, 1-(5-hydroxyhexyl)-3-methyl-7-propylxanthine and 3-methyl-1-(5-oxohexyl)-7-propylxanthine (=propentofylline), especially 3,7-dimethyl-1-(5-oxohexyl)xanthine (=pentoxifylline).

Particularly preferred compounds of the formula III are those compounds in which $R^5$ represents a methyl or ethyl group. Equally preferred are those compounds of the formula III in which only one of the two radicals $R^4$ or $R^6$ represents the tertiary hydroxyalkyl group defined above. Additionally preferred are those compounds in which $R^7$ represents a methyl group, and n denotes an integer from 3 to 5, so that the tertiary hydroxyalkyl radical IIIa represents either [(-1)-hydroxy-($\omega$-1)-methyl]-pentyl, -hexyl or -heptyl, especially those in which $R^5$ denotes methyl or ethyl.

In addition, worthy of particular emphasis are those compounds of the formula III in which $R^4$ represents the tertiary hydroxyalkyl group, and $R^6$ represents alkyl, hydroxyalkyl or alkoxyalkyl, having 1 to 4 carbon atoms in each case, such as, for example, 7-ethoxymethyl-1-(5-hydroxy-5-methylhexyl)-3-methylxanthine.

Another embodiment of the invention comprises using the oxoalkylxanthines of the formula I and II, or the hydroxyalkylxanthines of the formula I and III, not as such but in the form of a prodrug from which the therapeutically active xanthine compounds, having the substituents defined in formulae I, II and III, can be released only by bio-transformation in the body. Suitable for this purpose are, for example, the acetalized oxoalkylxanthines in which the carbonyl groups are replaced by the structural element of the formula IV

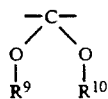
(IV)

and the O-acylated hydroxyalkylxanthines having the structural element of the formula (V)

$R^{11}$—CO—O—   (V)

in place of the hydroxyl group, where $R^9$ and $R^{10}$ each represents an alkyl group having up to 4 carbon atoms or together represent an ethylene, trimethylene or tetramethylene group, and $R^{11}$ denotes an alkyl radical having up to 4 carbon atoms or optionally substituted phenyl or pyridyl.

The ratio by weight of the substance releasing TNF to the xanthine derivative in the combination products according to the invention can cover a wide range. A ratio by weight of about 1:100 to about 100:1 is to be preferred, particularly preferably from about 1:10 to about 10:1.

The combination products according to the invention can be administered in a variety of ways. For example, they can be administered intravenously, intramuscularly, intraperitoneally, subcutaneously or orally.

The combination products according to the invention are prepared by converting the substance releasing TNF and at least one xanthine derivative, where appropriate with other additives and/or auxiliaries, into a suitable administration form. The additives or auxiliaries belong to the group of vehicles, preservatives and other customary auxiliaries. Examples of auxiliaries which can be used for oral administration forms are starch, for example potato, corn or wheat starch, cellulose or derivatives thereof, especially microcrystalline cellulose, silica, various sugars such as lactose, magnesium carbonate and/or calcium phosphates. In addition, it is advantageous to add to the oral administration forms auxiliaries which improve the tolerability of the medicaments, such as, for example, mucilage-formers and resins. To improve the tolerability, the medicaments can also be administered in the form of enteric capsules. Furthermore, it may be advantageous to add to the administration form, or to a component of the combination product, an agent to slow release, where appropriate in the form of permeable membranes, such as, for example, those based on cellulose or polystyrene resin, or ion exchangers.

It is surprising that the said xanthine derivatives, although they are cleared from the body after only a few hours, nevertheless are able to suppress the undesireable side effects of substances releasing TNF, even when the latter are excreted from the body only over a very long period. Thus, for example, amphotericin B is still detectable in the body after 12 hours, whereas a xanthine derivative such as pentoxifylline has been excreted from the body after only 3 to 4 hours. Despite this the TNF-inhibiting effect of the xanthine derivative is sufficient.

The TNF-inhibiting effect of xanthine derivatives has been detected experimentally in the following way:

In the case of amphotericin B, it has been shown that the highly toxic side effects of the substance derive from the release of TNF. The release of TNF in mouse serum can be detected by a specific ELISA method using murine monoclonal anti-TNF. Intraperitoneal administration of amphotericin B in amounts of 100 mg/kg or more to mice is found to be followed by 100% mortality. The experimental results compiled in the attached table show that the toxic effect of amphotericin B cannot be overcome even by dexamethasone. However, if amphotericin B is administered together with pentoxifylline, then all the mice which received 100 or 150 mg/kg amphotericin B survive when 100 mg/kg pentoxifylline is administered. Not until an excessive dose of 200 mg/kg amphotericin B is administered is it no longer possible to neutralize the side effects by administration of 100 mg/kg pentoxifylline.

| Amphotericin B mg/kg | Dexamethasone mg/kg | Pentoxifylline mg/kg | Day 0 | Day 1 | Day 2 | Day 3 | Day 4 | Day 5 | Day 6 | Day 7 |
|---|---|---|---|---|---|---|---|---|---|---|
| 100 | 0 | 0 | 0 | 40 | 100 | | | | | |
| 100 | 0 | 10 | 0 | 20 | 60 | 80 | 100 | | | |
| 100 | 0 | 50 | 0 | 20 | 40 | 60 | 60 | 60 | 60 | 60 |
| 100 | 0 | 100 | 0 | 0 | 0 | 0 | 0 | 0 | 0 | 0 |
| 100 | 100 | 0 | 0 | 0 | 0 | 20 | 40 | 40 | 40 | 40 |
| 150 | 0 | 0 | 0 | 100 | | | | | | |
| 150 | 0 | 10 | 0 | 40 | 100 | | | | | |
| 150 | 0 | 50 | 0 | 60 | 80 | 80 | 100 | | | |
| 150 | 0 | 100 | 0 | 0 | 0 | 0 | 0 | 0 | 0 | 0 |
| 200 | 0 | 0 | 100 | | | | | | | |
| 200 | 0 | 10 | 80 | 100 | | | | | | |
| 200 | 0 | 50 | 40 | 100 | | | | | | |
| 200 | 0 | 100 | 0 | 20 | 100 | | | | | |
| 200 | 100 | 0 | 0 | 100 | | | | | | |

We claim:

1. A pharmaceutical composition consisting essentially of (a) a pharmaceutical agent capable of stimulating the production of tumor necrosis factor and (b) a tumor necrosis factor inhibitor.

2. A pharmaceutical composition as claimed in claim 1, wherein said inhibitor is a xanthine derivative.

3. A pharmaceutical composition as claimed in claim 2, wherein said inhibitor is at least one of pentoxifylline and propentofylline.

4. A pharmaceutical composition as claimed in claim 1, wherein said inhibitor is a monoclonal antitumor necrosis factor antibody.

5. A pharmaceutical composition as claimed in claim 2, wherein said xanthine derivative is at least one selected from the group consisting of 1) A compound of the formula I

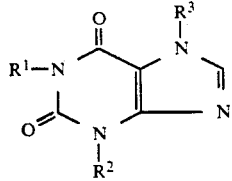

wherein one of $R^1$ and $R^3$ is a straight-chain alkyl, ($\omega$-1)-oxoalkyl or ($\omega$-1)-hydroxyalkyl group comprising 3 to 8 carbon atoms, and $R^2$ and $R^3$ or $R^1$ and $R^2$ are straight-chain or branched alkyl groups comprising 1 to 8 carbon atoms in the position of $R^1$ and $R^3$ and 1 to 4 carbon atoms in the position of $R^2$, and wherein the total number of carbon atoms in $R^2$ and $R^3$ or in $R^1$ and $R^2$ does not exceed 10, 2) A compound of the formula II

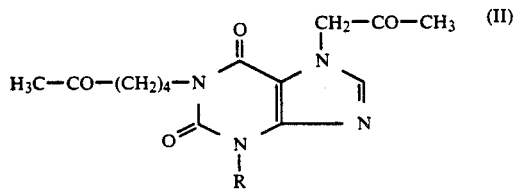

in which R is an alkyl group comprising 1 to 4 carbon atoms,

3) A compound of the formula III

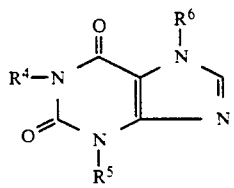

wherein at least one of $R^4$ and $R^6$ is a tertiary hydroxyalkyl group of the formula IIIa

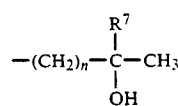

wherein $R^7$ is an alkyl group comprising up to 3 carbon atoms, and n is an integer from 2 to 5, provided that if only one of $R^4$ and $R^6$ is a tertiary hydroxyalkyl group, the other is a hydrogen atom or an aliphatic hydrocarbon group $R^8$, wherein $R^8$ comprises up to 6 carbon atoms which can be interrupted by up to 2 oxygen atoms or substituted by an oxo group or up to two hydroxyl groups, and wherein $R^5$ is an alkyl group having 1 to 4 carbon atoms, 4) A prodrug form of one of the compounds of formulas I to III, and 5) A metabolite of one of the compounds of formulas I to III.

6. A pharmaceutical composition as claimed in claim 5, wherein the xanthine derivative is a compound of formula I, and wherein $R^1$ or $R^3$ is a hexyl, 5-oxohexyl or 5-hydroxyhexyl group.

7. A pharmaceutical composition as claimed in claim 6, wherein said inhibitor is at least one selected from the group consisting of 1-hexyl-3,7-dimethylxanthine, 1-(5-hydroxyhexyl)-3,7-dimethylxanthine, 3,7-dimethyl-1-(5-oxohexyl)xanthine, 7-(5-hydroxyhexyl)-1,3-dimethylxanthine, 1,3-dimethyl-7-(5-oxohexyl)xanthine, 1-(5-hydroxyhexyl)-3-methyl-7-propylxanthine, 3-methyl-1-(5-oxohexyl)-7-propylxanthine, and 3,7-dimethyl-1-(5-oxohexyl)xanthine.

8. A pharmaceutical composition as claimed in claim 5, wherein the xanthine derivative is a compound of formula III, and wherein $R^5$ is a methyl or ethyl group.

9. A pharmaceutical composition as claimed in claim 5, wherein the xanthine derivative is a compound of formula III, and wherein $R^7$ is a methyl group and n is an integer from 3 to 5.

10. A pharmaceutical composition as claimed in claim 8, wherein the tertiary hydroxyalkyl group of formula IIIa is a [(-1)-hydroxy-(ω-1)-methyl]-pentyl, [(-1)-hydroxy-(ω-1)-methyl]-hexyl, or [(-1)-hydroxy-(ω-1)-methyl]-heptyl group.

11. A pharmaceutical composition as claimed in claim 5, wherein the xanthine derivative is a compound of formula III, and wherein $R^4$ is a tertiary hydroxyalkyl group, and $R^6$ is an alkyl, hydroxyalkyl, or alkoxyalkyl group, comprising 1 to 4 carbon atoms.

12. A pharmaceutical composition as claimed in claim 11, wherein said tumor necrosis factor inhibitor is 7-ethoxymethyl-1-(5-hydroxy-5-methylhexyl)-3-methylxanthine.

13. A pharmaceutical composition as claimed in claim 5, wherein said tumor necrosis factor inhibitor is a prodrug and is an acetalized oxoalkylxanthine comprising a carbonyl group that is replaced by a group of formula IV

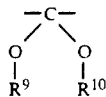

and a hydroxyl group that is replaced by an O-acylated hydroxyalkylxanthine group of formula V

wherein each of $R^9$ and $R^{10}$ is an alkyl group comprising up to 4 carbon atoms or together represent an ethylene, trimethylene or tetramethylene group, and $R^{11}$ is an alkyl group comprising up to 4 carbon atoms or is a substituted phenyl or pyridyl group.

14. A pharmaceutical composition as claimed in claim 1, wherein the ratio by weight of the agent capable of stimulating the production of tumor necrosis factor and the inhibitor is about 1:100 to about 100:1.

15. A pharmaceutical composition as claimed in claim 14, wherein said ratio is about 1:10 to about 10:1.

16. A pharmaceutical composition as claimed in claim 1, wherein said pharmaceutical agent is amphotericin B, and said inhibitor is pentoxiflylline.

17. A method for the stimulation of the production of tumor necrosis factor comprising administering to a warm-blooded animal a therapeutically effective amount of a pharmaceutical composition as claimed in claim 1.

18. A method as claimed in claim 17, wherein the pharmaceutical composition comprises a tumor necrosis factor inhibitor which is a xanthine derivative.

19. A method as claimed in claim 18, wherein the pharmaceutical composition comprises a pharmaceutical agent that is capable of stimulating the production of tumor necrosis factor, and the ratio by weight of the pharmaceutical agent to the tumor necrosis factor inhibitor is about 1:100 to about 100:1.

20. A method as claimed in claim 19, wherein the pharmaceutical agent is amphotericin B and the inhibitor is pentoxifylline.

* * * * *